United States Patent
Shah

(10) Patent No.: US 11,746,385 B2
(45) Date of Patent: Sep. 5, 2023

(54) METHODS OF DETECTING TUMOR PROGRESSION VIA ANALYSIS OF CELL-FREE NUCLEIC ACIDS

(71) Applicant: Lexent Bio, Inc., San Francisco, CA (US)

(72) Inventor: Abhik Shah, San Francisco, CA (US)

(73) Assignee: Lexent Bio, Inc., San Francisco, CA (US)

( * ) Notice: Subject to any disclaimer, the term of this patent is extended or adjusted under 35 U.S.C. 154(b) by 395 days.

(21) Appl. No.: 16/876,533

(22) Filed: May 18, 2020

(65) Prior Publication Data

US 2020/0377960 A1 Dec. 3, 2020

Related U.S. Application Data

(60) Provisional application No. 62/850,808, filed on May 21, 2019.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/156* (2013.01)

(58) Field of Classification Search
CPC ............ C12Q 1/6886; C12Q 2600/112; C12Q 2600/156
USPC .......................................................... 514/789
See application file for complete search history.

(56) References Cited

U.S. PATENT DOCUMENTS

2013/0150253 A1\* 6/2013 Deciu .................. C12Q 1/6883
506/2

\* cited by examiner

*Primary Examiner* — Yih-Horng Shiao
(74) *Attorney, Agent, or Firm* — MORRISON & FOERSTER LLP

(57) ABSTRACT

The present disclosure provides methods of assessing tumor progression in a subject. In an aspect, a method for assessing tumor progression of a subject can comprise: measuring a count of a plurality of cell-free DNA (cfDNA) molecules at each of a plurality of genomic regions, wherein the plurality of cfDNA molecules is obtained or derived from a bodily fluid sample of the subject; processing the counts measured at each of the genomic regions to obtain quantitative measures of deviation of the counts relative to a plurality of reference values, to produce deviation scores; determining a difference between the deviation scores and a plurality of reference deviation scores to produce changes in deviation (CID) values, and calculating a CID score based on the CID values; and detecting a tumor progression of the subject when the CID score satisfies a pre-determined criterion.

41 Claims, 2 Drawing Sheets

METHODS OF DETECTING TUMOR PROGRESSION VIA ANALYSIS OF CELL-FREE NUCLEIC ACIDS

CROSS-REFERENCE

This application claims the benefit of U.S. Provisional Patent Application No. 62/850,808, filed May 21, 2019, which is entirely incorporated herein by reference.

BACKGROUND

Tumor progression may generally refer to cases in which subjects (e.g., patients) with cancer have a tumor that is progressing in severity (e.g., tumor burden, tumor size, cancer stage). For example, tumor progression in a patient may be an indication that the patient's tumor is not responsive to a therapeutic regimen for the cancer. On the other hand, tumor non-progression in a patient may be an indication that the patient's tumor is responding to a therapeutic regimen for the cancer. In addition, the tumor progression or tumor non-progression status of a patient may be indicative of a prognosis of a subject for cancer treatments.

SUMMARY

Methods and systems are provided for assessing tumor progression of a subject, such as a patient with cancer, by analyzing a bodily fluid sample (e.g., blood sample) of the subject. Tumor progression or tumor non-progression may be assessed and/or monitored by analyzing tumor DNA (e.g., from cell-free DNA) from a sample of a subject at a plurality of genomic regions, and measuring a number of counts of the DNA molecules at each of the plurality of genomic regions based on the analysis of the tumor DNA. The tumor progression or tumor non-progression status of a subject may be indicative of a diagnosis, prognosis, or treatment selection for a subject.

In some embodiments, a tumor progression or tumor non-progression may vary (e.g., increase or decrease) over a duration of time (e.g., over two or more different time points). In some embodiments, this duration of time may correspond to, e.g., a course of treatment for the cancer of the subject or a monitoring period after surgical resection or other treatment of a tumor for (e.g., to detect recurrence of the tumor in the subject). In some embodiments, determination of a tumor progression or tumor non-progression status may comprise generating a quantitative measure of cfDNA sequencing reads for each of a plurality of genomic regions. The plurality of genomic regions may comprise tumor markers. In some cases, the quantitative measure of cfDNA (e.g., sequencing reads) may comprise a count of sequencing reads that align with each of the plurality of genomic regions. Alternatively, obtaining the quantitative measure of cfDNA may comprise performing binding measurements of the plurality of cfDNA molecules at each of the plurality of genomic regions. In some embodiments, determination of a tumor progression or tumor non-progression status may comprise generating a comparison (e.g., a difference or a ratio) of quantitative measures for cfDNA (e.g., sequencing reads). By assessing a comparison of counts of sequencing reads across different sets of genomic regions, methods provided herein may allow determination of tumor progression or tumor non-progression statuses, which can be useful for diagnosis, prognosis, or treatment selection for a subject through a non-invasive lab test (e.g., a blood based test).

In an aspect, the present disclosure provides a method for assessing tumor progression of a subject, comprising: measuring a count of a plurality of cell-free DNA (cfDNA) molecules at each of a plurality of genomic regions, wherein the plurality of cfDNA molecules is obtained or derived from a bodily fluid sample of the subject at a first timepoint; processing the plurality of counts measured at each of the plurality of genomic regions to obtain quantitative measures of deviation of the plurality of counts relative to a plurality of reference values, to produce a plurality of deviation scores; determining a difference between the plurality of deviation scores and a plurality of reference deviation scores to produce a plurality of changes in deviation (CID) values, and applying a logarithmic transformation to a sum of the plurality of CID values to produce a CID score; and detecting a tumor progression of the subject when the CID score satisfies a pre-determined criterion.

In some embodiments, the bodily fluid sample is selected from the group consisting of: blood, serum, plasma, vitreous, sputum, urine, tears, perspiration, saliva, semen, mucosal excretions, mucus, spinal fluid, cerebrospinal fluid (CSF), pleural fluid, peritoneal fluid, amniotic fluid, and lymph fluid. In some embodiments, measuring the plurality of counts comprises sequencing the plurality of cfDNA molecules to generate sequencing reads at each of the plurality of genomic regions in the plurality of cfDNA molecules. In some embodiments, the sequencing comprises whole genome sequencing (WGS). In some embodiments, the sequencing comprises whole genome bisulfite sequencing (WGBS), whole exome sequencing, or whole epigenome sequencing. In some embodiments, the sequencing is performed at a depth of no more than about 40×. In some embodiments, the sequencing is performed at a depth of no more than about 30×. In some embodiments, the sequencing is performed at a depth of no more than about 25×. In some embodiments, the sequencing is performed at a depth of no more than about 20×. In some embodiments, the sequencing is performed at a depth of no more than about 12×. In some embodiments, the sequencing is performed at a depth of no more than about 10×. In some embodiments, the sequencing is performed at a depth of no more than about 8×. In some embodiments, the sequencing is performed at a depth of no more than about 6×. In some embodiments, the sequencing is performed at a depth of no more than about 5×, no more than about 4×, no more than about 3×, no more than about 2×, or no more than about 1×.

In some embodiments, the method further comprises aligning the plurality of sequence reads to a reference genome, thereby producing a plurality of aligned sequence reads. In some embodiments, measuring the plurality of counts comprises performing binding measurements of the plurality of cfDNA molecules at each of the plurality of genomic regions. In some embodiments, the method further comprises enriching the plurality of cfDNA molecules for at least a subset of the plurality of genomic regions. In some embodiments, the enrichment comprises amplifying the plurality of cfDNA molecules. In some embodiments, the amplification comprises selective amplification. In some embodiments, the amplification comprises universal amplification. In some embodiments, the enrichment comprises selectively isolating at least a portion of the plurality of cfDNA molecules. In some embodiments, selectively isolating the at least the portion of the plurality of cfDNA molecules comprises using a plurality of probes, each of the plurality of probes having sequence complementarity with at least a portion of a genomic region of the plurality of genomic regions. In some embodiments, the at least the portion comprises a tumor marker locus. In some embodiments, the at least the portion comprises a plurality of tumor marker loci. In some embodiments, the plurality of tumor marker loci comprises one or more loci having copy number alteration (e.g., CNA loci such as MET, EGFR, and BRCA2). Such CNA loci may be found using databases such as The Cancer Genome Atlas (TCGA) and the Catalogue of Somatic Mutations in Cancer (COSMIC).

In some embodiments, measuring the plurality of counts comprises counting a number of the plurality of sequence reads aligning to each of the plurality of genomic regions. In some embodiments, the method further comprises correcting the plurality of counts for GC content and/or mappability bias. In some embodiments, the correcting comprises using a LOESS regression. In some embodiments, the plurality of reference values comprises an additional plurality of counts obtained from additional cfDNA molecules obtained or derived from additional bodily fluid samples of additional subjects. In some embodiments, the additional subjects are subjects without cancer (e.g., subjects unaffected by cancer or subjects without a diagnosis of cancer). In some embodiments, the plurality of reference deviation scores are obtained using additional bodily fluid samples of the subject obtained at one or more subsequent time points after the first timepoint.

In some embodiments, the quantitative measure of deviation is a statistical measure of deviation of the plurality of counts relative to the plurality of reference values, or a weighted combination thereof. In some embodiments, the method further comprises filtering out a subset of the plurality of CID values that meet a pre-determined criterion. In some embodiments, the method further comprises filtering out a CID value of the plurality of CID values when the difference between the deviation score and the reference deviation score comprises a difference of no more than about 1 standard deviation. In some embodiments, the method further comprises filtering out a CID value of the plurality of CID values when the difference between the deviation score and the reference deviation score comprises a difference of no more than about 2 standard deviations. In some embodiments, the method further comprises filtering out a CID value of the plurality of CID values when the difference between the deviation score and the reference deviation score comprises a difference of no more than about 3 standard deviations.

In some embodiments, the method further comprises calculating a sum of the filtered plurality of CID values. In some embodiments, calculating the sum comprises calculating a weighted sum of the filtered plurality of CID values. In some embodiments, determining the difference comprises calculating a subtraction between each of the plurality of deviation scores and a corresponding reference deviation score of the plurality of reference deviation scores. In some embodiments, the method further comprises dividing each of the plurality of deviation scores or the plurality of CID values by a corresponding median absolute deviance of the plurality of reference values. In some embodiments, the additional subjects comprise one or more subjects without a tumor. In some embodiments, the additional subjects comprise one or more subjects not having tumor progression.

In some embodiments, the plurality of genomic regions comprises non-overlapping genomic regions of a reference genome having a pre-determined size. In some embodiments, the pre-determined size is about 50 kilobases (kb), about 100 kb, about 200 kb, about 500 kb, about 1 megabases (Mb), about 2 Mb, about 5 Mb, or about 10 Mb. In some embodiments, the plurality of genomic regions excludes genomic regions of the reference genome corresponding to one or more of: sex chromosomes, chromosome 19, centromere regions in each chromosome, and telomere regions in each chromosome.

In some embodiments, the plurality of genomic regions comprises at least about 1,000 distinct genomic regions. In some embodiments, the plurality of genomic regions comprises at least about 2,000 distinct genomic regions. In some embodiments, the plurality of genomic regions comprises at least about 3,000 distinct genomic regions, at least about 4,000 distinct genomic regions, at least about 5,000 distinct genomic regions, at least about 6,000 distinct genomic regions, at least about 7,000 distinct genomic regions, at least about 8,000 distinct genomic regions, at least about 9,000 distinct genomic regions, at least about 10,000 distinct genomic regions, at least about 15,000 distinct genomic regions, at least about 20,000 distinct genomic regions, at least about 25,000 distinct genomic regions, at least about 30,000 distinct genomic regions, at least about 35,000 distinct genomic regions, at least about 40,000 distinct genomic regions, at least about 45,000 distinct genomic regions, at least about 50,000 distinct genomic regions, at least about 100,000 distinct genomic regions, at least about 150,000 distinct genomic regions, at least about 200,000 distinct genomic regions, at least about 250,000 distinct genomic regions, at least about 300,000 distinct genomic regions, at least about 400,000 distinct genomic regions, or at least about 500,000 distinct genomic regions.

In some embodiments, the method further comprises detecting the tumor progression of the subject when the CID score is greater than zero. In some embodiments, the method further comprises detecting the tumor progression of the subject with a sensitivity of at least about 50%, at least about 55%, at least about 60%, at least about 65%, at least about 70%, at least about 75%, at least about 80%, at least about 85%, at least about 90%, at least about 91%, at least about 92%, at least about 93%, or at least about 94%. In some embodiments, the method further comprises detecting the tumor progression of the subject with a sensitivity of at least about 95%, at least about 96%, at least about 97%, or at least about 98%. In some embodiments, the method further comprises detecting the tumor progression of the subject with a sensitivity of at least about 99%. In some embodiments, the method further comprises detecting the tumor progression of the subject with a specificity of at least about 50%, at least about 55%, at least about 60%, at least about 65%, at least about 70%, at least about 75%, at least about 80%, at least about 85%, at least about 90%, at least about 91%, at least about 92%, at least about 93%, or at least about 94%. In some embodiments, the method further comprises detecting the tumor progression of the subject with a specificity of at least about 95%, at least about 96%, at least about 97%, or at least about 98%. In some embodiments, the method further comprises detecting the tumor progression of the subject with a specificity of at least about 99%.

In some embodiments, the method further comprises detecting the tumor progression of the subject with a positive predictive value (PPV) of at least about 50%, at least about 55%, at least about 60%, at least about 65%, at least about 70%, at least about 75%, at least about 80%, at least about 85%, at least about 90%, at least about 91%, at least about 92%, at least about 93%, or at least about 94%. In some embodiments, the method further comprises detecting the tumor progression of the subject with a positive predictive value (PPV) of at least about 95%, at least about 96%, at least about 97%, or at least about 98%. In some embodiments, the method further comprises detecting the tumor progression of the subject with a positive predictive value (PPV) of at least about 99%. In some embodiments, the method further comprises detecting the tumor progression of the subject with a negative predictive value (NPV) of at least about 50%, at least about 55%, at least about 60%, at least about 65%, at least about 70%, at least about 75%, at least about 80%, at least about 85%, at least about 90%, at least about 91%, at least about 92%, at least about 93%, or at least about 94%. In some embodiments, the method further comprises detecting the tumor progression of the subject with a negative predictive value (NPV) of at least about 95%, at least about 96%, at least about 97%, or at least about 98%. In some embodiments, the method further comprises detecting the tumor progression of the subject with a negative predictive value (NPV) of at least about 99%.

In some embodiments, the method further comprises detecting the tumor progression of the subject with an area under the curve (AUC) of at least about 0.50, at least about 0.55, at least about 0.60, at least about 0.65, at least about 0.70, at least about 0.75, at least about 0.80, at least about 0.85, at least about 0.90, at least about 0.91, at least about 0.92, at least about 0.93, or at least about 0.94. In some embodiments, the method further comprises detecting the tumor progression of the subject with an area under the curve (AUC) of at least about 0.95, at least about 0.96, at least about 0.97, or at least about 0.98. In some embodiments, the method further comprises detecting the tumor progression of the subject with an area under the curve (AUC) of at least about 0.99.

In some embodiments, the method further comprises determining a tumor non-progression of the subject when the CID score does not satisfy the pre-determined criterion. In some embodiments, the method further comprises detecting the tumor non-progression of the subject when the CID score is zero.

In some embodiments, the subject has been diagnosed with cancer. In some embodiments, the method further comprises, based on the determined tumor progression of the subject, administering a therapeutically effective dose of a treatment to treat the cancer of the subject. In some embodiments, the treatment comprises surgery, chemotherapy, radiation therapy, targeted therapy, or immunotherapy.

In another aspect, the present disclosure provides a system, comprising a controller comprising or capable of accessing, a non-transitory computer-readable medium comprising machine-executable instructions which, upon execution by one or more computer processors, perform a method for assessing tumor progression of a subject, the method comprising: measuring a count of a plurality of cell-free DNA (cfDNA) molecules at each of a plurality of genomic regions, wherein the plurality of cfDNA molecules is obtained or derived from a bodily fluid sample of the subject at a first timepoint; processing the plurality of counts measured at each of the plurality of genomic regions to obtain quantitative measures of deviation of the plurality of counts relative to a plurality of reference values, to produce a plurality of deviation scores; determining a difference between the plurality of deviation scores and a plurality of reference deviation scores to produce a plurality of changes in deviation (CID) values, and applying a logarithmic transformation to a sum of the plurality of CID values to produce a CID score; and detecting a tumor progression of the subject when the CID score satisfies a pre-determined criterion.

In another aspect, the present disclosure provides a non-transitory computer-readable medium comprising machine-executable instructions which, upon execution by one or more computer processors, perform a method for assessing tumor progression of a subject, the method comprising: measuring a count of a plurality of cell-free DNA (cfDNA) molecules at each of a plurality of genomic regions, wherein the plurality of cfDNA molecules is obtained or derived from a bodily fluid sample of the subject at a first timepoint; processing the plurality of counts measured at each of the plurality of genomic regions to obtain quantitative measures of deviation of the plurality of counts relative to a plurality of reference values, to produce a plurality of deviation scores; determining a difference between the plurality of deviation scores and a plurality of reference deviation scores to produce a plurality of changes in deviation (CID) values, and applying a logarithmic transformation to a sum of the plurality of CID values to produce a CID score; and detecting a tumor progression of the subject when the CID score satisfies a pre-determined criterion.

In another aspect, the present disclosure provides a method for assessing tumor progression of a subject, comprising: measuring a count of a plurality of cell-free DNA (cfDNA) molecules at each of a plurality of genomic regions, wherein the plurality of cfDNA molecules is obtained or derived from a bodily fluid sample of the subject at a first timepoint; processing the plurality of counts measured at each of the plurality of genomic regions to obtain quantitative measures of deviation of the plurality of counts relative to a plurality of reference values, to produce a plurality of deviation scores, wherein the quantitative measures of deviation are statistical measures of deviation of the plurality of counts relative to the plurality of reference values, or a weighted combination thereof; determining a difference between the plurality of deviation scores and a plurality of reference deviation scores to produce a plurality of changes in deviation (CID) values; filtering out a subset of the plurality of CID values based at least in part on the determined differences, and calculating a CID score based on the plurality of filtered CID values; and detecting a tumor progression of the subject when the CID score satisfies a pre-determined criterion.

In another aspect, the present disclosure provides a system, comprising a controller comprising or capable of accessing, a non-transitory computer-readable medium comprising machine-executable instructions which, upon execution by one or more computer processors, perform a method for assessing tumor progression of a subject, the method comprising: measuring a count of a plurality of cell-free DNA (cfDNA) molecules at each of a plurality of genomic regions, wherein the plurality of cfDNA molecules is obtained or derived from a bodily fluid sample of the subject at a first timepoint; processing the plurality of counts measured at each of the plurality of genomic regions to obtain quantitative measures of deviation of the plurality of counts relative to a plurality of reference values, to produce a plurality of deviation scores, wherein the quantitative measures of deviation are statistical measures of deviation of the plurality of counts relative to the plurality of reference values, or a weighted combination thereof; determining a difference between the plurality of deviation scores and a plurality of reference deviation scores to produce a plurality of changes in deviation (CID) values; filtering out a subset of the plurality of CID values based at least in part on the determined differences, and calculating a CID score based on the plurality of filtered CID values; and detecting a tumor progression of the subject when the CID score satisfies a pre-determined criterion.

In another aspect, the present disclosure provides a non-transitory computer-readable medium comprising machine-executable instructions which, upon execution by one or more computer processors, perform a method for assessing tumor progression of a subject, the method comprising: measuring a count of a plurality of cell-free DNA (cfDNA) molecules at each of a plurality of genomic regions, wherein the plurality of cfDNA molecules is obtained or derived from a bodily fluid sample of the subject at a first timepoint; processing the plurality of counts measured at each of the plurality of genomic regions to obtain quantitative measures of deviation of the plurality of counts relative to a plurality of reference values, to produce a plurality of deviation scores, wherein the quantitative measures of deviation are statistical measures of deviation of the plurality of counts relative to the plurality of reference values, or a weighted combination thereof; determining a difference between the plurality of deviation scores and a plurality of reference deviation scores to produce a plurality of changes in deviation (CID) values; filtering out a subset of the plurality of CID values based at least in part on the determined differences, and calculating a CID score based on the plurality of filtered CID values; and detecting a tumor progression of the subject when the CID score satisfies a pre-determined criterion.

In another aspect, the present disclosure provides a method for assessing tumor progression of a subject, comprising: measuring a count of a plurality of cell-free DNA (cfDNA) molecules at each of a plurality of genomic regions, wherein the plurality of cfDNA molecules is obtained or derived from a bodily fluid sample of the subject at a first timepoint; assessing the plurality of counts measured at each of the plurality of genomic regions to obtain quantitative measures of deviation of the plurality of counts relative to a plurality of reference values, to produce a plurality of deviation scores; determining a difference between the plurality of deviation scores and a plurality of reference deviation scores to produce a plurality of changes in deviation (CID) values, and calculating a CID score based on the plurality of CID values; and detecting a tumor progression of the subject when the CID score satisfies a pre-determined criterion.

In another aspect, the present disclosure provides a system, comprising a controller comprising or capable of accessing, a non-transitory computer-readable medium comprising machine-executable instructions which, upon execution by one or more computer processors, perform a method for assessing tumor progression of a subject, the method comprising: measuring a count of a plurality of cell-free DNA (cfDNA) molecules at each of a plurality of genomic regions, wherein the plurality of cfDNA molecules is obtained or derived from a bodily fluid sample of the subject at a first timepoint; assessing the plurality of counts measured at each of the plurality of genomic regions to obtain quantitative measures of deviation of the plurality of counts relative to a plurality of reference values, to produce a plurality of deviation scores; determining a difference between the plurality of deviation scores and a plurality of reference deviation scores to produce a plurality of changes in deviation (CID) values, and calculating a CID score based on the plurality of CID values; and detecting a tumor progression of the subject when the CID score satisfies a pre-determined criterion.

In another aspect, the present disclosure provides a non-transitory computer-readable medium comprising machine-executable instructions which, upon execution by one or more computer processors, perform a method for assessing tumor progression of a subject, the method comprising: measuring a count of a plurality of cell-free DNA (cfDNA) molecules at each of a plurality of genomic regions, wherein the plurality of cfDNA molecules is obtained or derived from a bodily fluid sample of the subject at a first timepoint; assessing the plurality of counts measured at each of the plurality of genomic regions to obtain quantitative measures of deviation of the plurality of counts relative to a plurality of reference values, to produce a plurality of deviation scores; determining a difference between the plurality of deviation scores and a plurality of reference deviation scores to produce a plurality of changes in deviation (CID) values, and calculating a CID score based on the plurality of CID values; and detecting a tumor progression of the subject when the CID score satisfies a pre-determined criterion.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
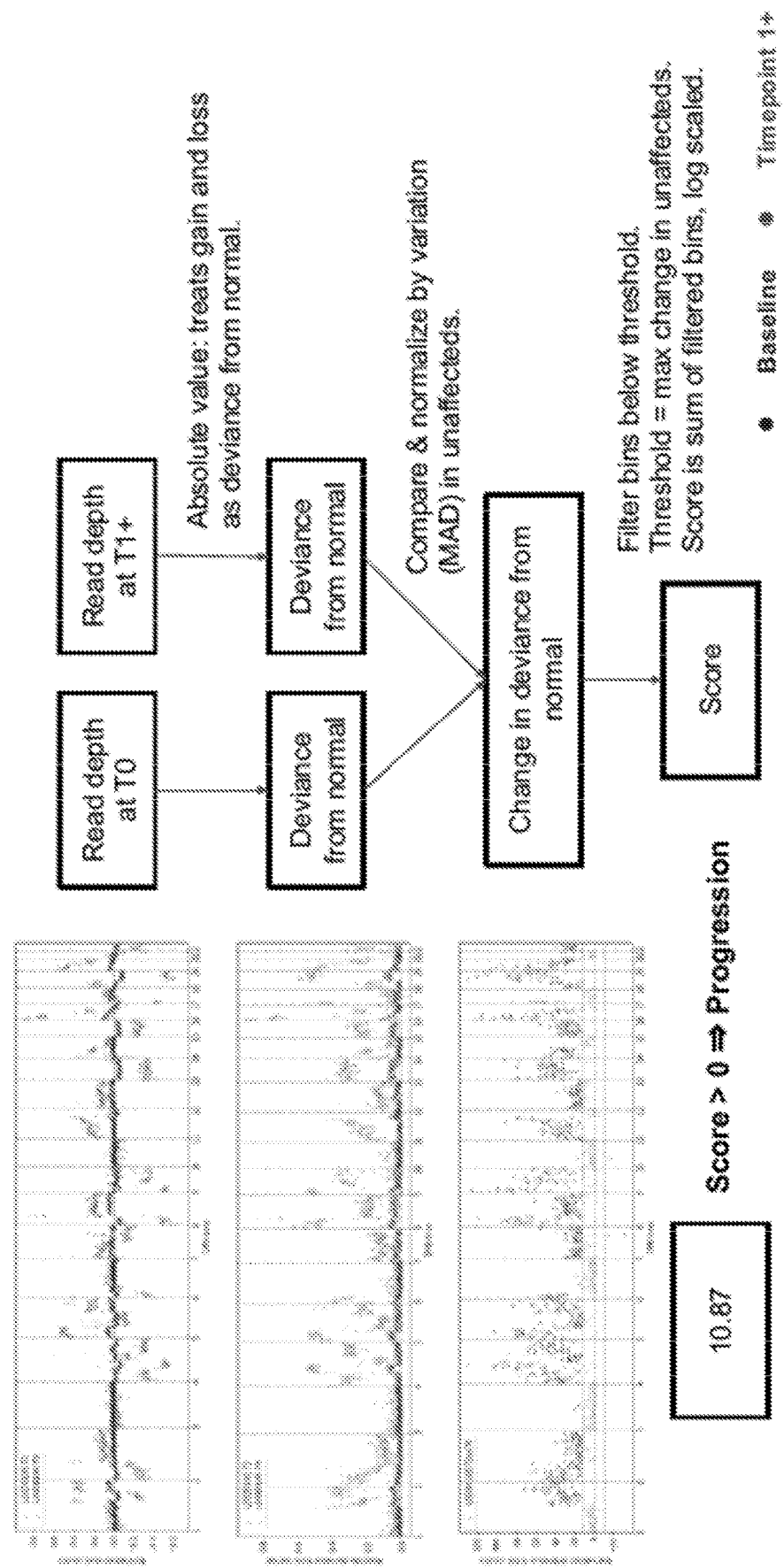
FIG. 1 illustrates an example method of assessing tumor progression in a subject using a Change in Deviation (CID) score, in accordance with some embodiments.

The term "nucleic acid," or "polynucleotide," as used herein, generally refers to a molecule comprising one or more nucleic acid subunits, or nucleotides. A nucleic acid may include one or more nucleotides selected from adenosine (A), cytosine (C), guanine (G), thymine (T) and uracil (U), or variants thereof. A nucleotide generally includes a nucleoside and at least 1, 2, 3, 4, 5, 6, 7, 8, 9, 10, or more phosphate (P03) groups. A nucleotide can include a nucleobase, a five-carbon sugar (either ribose or deoxyribose), and one or more phosphate groups, individually or in combination.

Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate (dNTP), which can be selected from deoxyadenosine triphosphate (dATP), deoxycytidine triphosphate (dCTP), deoxyguanosine triphosphate (dGTP), uridine triphosphate (dUTP) and deoxythymidine triphosphate (dTTP) dNTPs, that include detectable tags, such as luminescent tags or markers (e.g., fluorophores). A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). In some examples, a nucleic acid is deoxyribonucleic acid (DNA), ribonucleic acid (RNA), or derivatives or variants thereof. A nucleic acid may be single-stranded or double stranded. A nucleic acid molecule may be linear, curved, or circular or any combination thereof.

The terms "nucleic acid molecule," "nucleic acid sequence," "nucleic acid fragment," "oligonucleotide" and "polynucleotide," as used herein, generally refer to a polynucleotide that may have various lengths, such as either deoxyribonucleotides or ribonucleotides (RNA), or analogs thereof. A nucleic acid molecule can have a length of at least about 5 bases, 10 bases, 20 bases, 30 bases, 40 bases, 50 bases, 60 bases, 70 bases, 80 bases, 90, 100 bases, 110 bases, 120 bases, 130 bases, 140 bases, 150 bases, 160 bases, 170 bases, 180 bases, 190 bases, 200 bases, 300 bases, 400 bases, 500 bases, 1 kilobase (kb), 2 kb, 3, kb, 4 kb, 5 kb, 10 kb, or 50 kb or it may have any number of bases between any two of the aforementioned values. An oligonucleotide is typically composed of a specific sequence of four nucleotide bases: adenine (A); cytosine (C); guanine (G); and thymine (T) (uracil (U) for thymine (T) when the polynucleotide is RNA). Thus, the terms "nucleic acid molecule," "nucleic acid sequence," "nucleic acid fragment," "oligonucleotide" and "polynucleotide" are at least in part intended to be the alphabetical representation of a polynucleotide molecule. Alternatively, the terms may be applied to the polynucleotide molecule itself. This alphabetical representation can be input into databases in a computer having a central processing unit and/or used for bioinformatics applications such as functional genomics and homology searching. Oligonucleotides may include one or more nonstandard nucleotide(s), nucleotide analog(s) and/or modified nucleotides.

The term "sample," as used herein, generally refers to a biological sample. Examples of biological samples include nucleic acid molecules, amino acids, polypeptides, proteins, carbohydrates, fats, or viruses. In an example, a biological sample is a nucleic acid sample including one or more nucleic acid molecules. The nucleic acid molecules may be cell-free or cell-free nucleic acid molecules, such as cell-free DNA (cfDNA) or cell-free RNA (cfRNA). The nucleic acid molecules may be derived from a variety of sources including human, mammal, non-human mammal, ape, monkey, chimpanzee, reptilian, amphibian, or avian, sources. Further, samples may be extracted from a variety of animal fluids containing cell-free sequences, including but not limited to bodily fluid samples such as blood, serum, plasma, vitreous, sputum, urine, tears, perspiration, saliva, semen, mucosal excretions, mucus, spinal fluid, cerebrospinal fluid (CSF), pleural fluid, peritoneal fluid, amniotic fluid, lymph fluid, and the like. Cell free polynucleotides (e.g., cfDNA) may be fetal in origin (via fluid taken from a pregnant subject), or may be derived from tissue of the subject itself.

The term "subject," as used herein, generally refers to an individual having a biological sample that is undergoing processing or analysis. A subject can be an animal or plant. The subject can be a mammal, such as a human, dog, cat, horse, pig or rodent. The subject can be a patient, e.g., have or be suspected of having a disease, such as one or more cancers (e.g., brain cancer, breast cancer, cervical cancer, colorectal cancer, endometrial cancer, esophageal cancer, gastric cancer, hepatobiliary tract cancer, leukemia, liver cancer, lung cancer, lymphoma, ovarian cancer, pancreatic cancer, skin cancer, urinary tract cancer), one or more infectious diseases, one or more genetic disorder, or one or more tumors, or any combination thereof. For subjects having or suspected of having one or more tumors, the tumors may be of one or more types.

The term "whole blood," as used herein, generally refers to a blood sample that has not been separated into sub-components (e.g., by centrifugation). The whole blood of a blood sample may contain cfDNA and/or germline DNA. Whole blood DNA (which may contain cfDNA and/or germline DNA) may be extracted from a blood sample. Whole blood DNA sequencing reads (which may contain cfDNA sequencing reads and/or germline DNA sequencing reads) may be extracted from whole blood DNA.

The term "change in deviation" (CID) score, as used herein, generally refers to a quantitative measure of tumor progression or tumor non-progression of a subject, based at least in part on an analysis performed on a distribution of read counts generated (e.g., by a sequencing approach such as whole genome sequencing) from one or more cell-free samples obtained or derived from the subject. For example, such an analysis may be a longitudinal analysis, whereby cell-free samples are assayed at each of a set of multiple timepoints and a longitudinal comparison of the resulting distributions of read counts generated from the cell-free samples is determined. In some embodiments, the CID score is calculated using a set of deviation values, which may be calculated relative to a set of reference values (e.g., a baseline set of deviation values generated from unaffected subjects). As an example, the CID score can be calculated using two sets of deviation values (e.g., obtained at two different timepoints), by calculating a set of changes (e.g., differences) in deviation values across the two different timepoints. As another example, the CID score can be calculated using a set of deviation values and a set of reference deviation values, by calculating a set of changes (e.g., differences) between the deviation values and the reference deviation values. In some embodiments, the CID score is calculated relative to an earlier CID score of the subject (e.g., a baseline generated at an initial timepoint or a most recent CID score) or relative to an earlier set of deviation values of the subject.

Assessing Tumor Progression in DNA Sequence Data from a Subject

Assessment of tumor progression may be relatively straightforward when a significant portion (e.g., greater than about 80%) of a sample taken from a subject comes from or is derived from tumor cells. However, in a cell free DNA (cfDNA) preparation from a subject's plasma derived from a blood sample, the detection of tumor DNA from the cfDNA and the assessment of tumor progression therefrom may be an insensitive and noisy process. Detection of tumor DNA and assessment of tumor progression from such insensitive and/or noisy signals may be challenging due to the overwhelming signal from non-tumor DNA (e.g., from germline DNA from germline cells that are not tumor derived). The present disclosure provides methods and systems for assessing tumor progression from cell-free DNA (cfDNA) sequence data (e.g., cfDNA sequencing reads) or binding measurements of cfDNA molecules derived from a sample of a subject. Once cfDNA sequence data has been received from analysis of a sample from the subject, one or more bioinformatics processes may be used to assess tumor progression or tumor non-progression of the subject.

In an aspect, the present disclosure provides a method for assessing tumor progression of a subject, comprising: measuring a count of a plurality of cell-free DNA (cfDNA) molecules at each of a plurality of genomic regions, wherein the plurality of cfDNA molecules is obtained or derived from a blood sample of the subject; processing the plurality of counts measured at each of the plurality of genomic regions to obtain a quantitative measure of deviation of the counts, wherein the processing comprises normalizing the plurality of counts against an additional plurality of counts obtained from additional cfDNA molecules obtained or derived from additional blood samples of additional subjects; and detecting a tumor progression of the subject when the quantitative measure of deviation of the counts satisfies a pre-determined criterion.

FIG. 1 illustrates an example method of assessing tumor progression in a subject using a Change in Deviation (CID) score, in accordance with some embodiments. In some embodiments, read counts are measured from a plurality of cell-free DNA (cfDNA) molecules obtained from or derived from a sample of a subject. In some embodiments, measuring the plurality of read counts comprises sequencing the plurality of cfDNA molecules to generate sequencing reads at each of the plurality of genomic regions in the plurality of cfDNA molecules. After the plurality of read counts is measured, an absolute deviation (or deviance) of the read counts measured from cfDNA molecules of unaffected subjects (e.g., relative to read counts generated from samples of normal subjects without cancer) is generated for each of the plurality of genomic regions. These values of absolute deviance from normal may be calculated using an absolute difference between each read count and the corresponding mean or median read count of the normal read counts. As another example, the values of absolute deviance from normal may be calculated using a "robust z-score" generated based on a median absolute deviation (MAD), which is obtained by assaying samples obtained from an unaffected cohort of subjects. For example, such a "robust z-score" may be generated by determining an absolute difference between each read count and the corresponding mean or median read count of the unaffected/normal read counts, and dividing the absolute difference by the median absolute deviation (MAD) of the unaffected cohort. For longitudinal analysis, this absolute deviance calculation may be repeated for the same subject at each of a plurality of timepoints (e.g., a baseline sample taken at time T0, and subsequent samples taken at subsequent times T1, T2, etc.), and the absolute deviance values at such timepoints may be compared and normalized by the variation in unaffected subjects. The CID score may be obtained by filtering bins below a threshold given by the maximum change among the unaffected subjects and computing a log-scaled sum of the filtered bins. A positive CID score may be indicative of tumor progression.

For example, sequencing reads may be generated from the cfDNA using any suitable sequencing method known to one of skill in the art. The sequencing method can be a first-generation sequencing method, such as Maxam-Gilbert or Sanger sequencing, or a high-throughput sequencing (e.g., next-generation sequencing or NGS) method. A high-throughput sequencing method may sequence simultaneously (or substantially simultaneously) at least 10,000, 100,000, 1 million, 10 million, 100 million, 1 billion, or more polynucleotide molecules. Sequencing methods may include, but are not limited to: pyrosequencing, sequencing-by-synthesis, single-molecule sequencing, nanopore sequencing, semiconductor sequencing, sequencing-by-ligation, sequencing-by-hybridization, Digital Gene Expression (Helicos), massively parallel sequencing, e.g., Helicos, Clonal Single Molecule Array (Solexa/Illumina), sequencing using PacBio, SOLiD, Ion Torrent, or Nanopore platforms.

In some embodiments, the sequencing comprises whole genome sequencing (WGS). The sequencing may be performed at a depth sufficient to assess tumor progression or tumor non-progression in a subject with a desired performance (e.g., accuracy, sensitivity, specificity, positive predictive value (PPV), negative predictive value (NPV), or the area under curve (AUC) of a receiver operator characteristic (ROC)). In some embodiments, the sequencing is performed in a "low-pass" manner, for example, at a depth of no more than about 12×, no more than about 11×, no more than about 10×, no more than about 9×, no more than about 8×, no more than about 7×, no more than about 6×, no more than about 5×, no more than about 4×, no more than about 3.5×, no more than about 3×, no more than about 2.5×, no more than about 2×, no more than about 1.5×, or no more than about 1×.

In some embodiments, assessing tumor progression or tumor non-progression in a subject may comprise aligning the cfDNA sequencing reads to a reference genome. The reference genome may comprise at least a portion of a genome (e.g., the human genome). The reference genome may comprise an entire genome (e.g., the entire human genome). The reference genome may comprise a database comprising a plurality of genomic regions that correspond to coding and/or non-coding genomic regions of a genome. The database may comprise a plurality of genomic regions that correspond to cancer-associated (or tumor-associated) coding and/or non-coding genomic regions of a genome, such as cancer driver mutations (e.g., single nucleotide variants (SNVs), copy number variants (CNVs), insertions or deletions (indels), fusion genes, and genomic regions (such as mononucleotides and/or dinucleotides)). The alignment may be performed using a Burrows-Wheeler algorithm or any other alignment algorithm known to one of skill in the art.

In some embodiments, assessing tumor progression or tumor non-progression in a subject may comprise generating a quantitative measure of the cfDNA sequencing reads for each of a plurality of genomic regions. Quantitative measures of the cfDNA sequencing reads may be generated, such as counts of DNA sequencing reads that are aligned with a given genomic region. CfDNA sequencing reads having a portion or all of the sequencing read aligning with a given genomic region may be counted toward the quantitative measure for that genomic region.

In some embodiments, genomic regions may comprise tumor markers. Patterns of specific and non-specific genomic regions may be indicative of tumor progression or tumor non-progression status. Changes over time in these patterns of genomic regions may be indicative of changes in tumor progression or tumor non-progression status.

In some embodiments, measuring the plurality of counts comprises performing binding measurements of the plurality of cfDNA molecules at each of the plurality of genomic regions. In some embodiments, performing the binding measurements comprises assaying the plurality of cfDNA molecules using probes that are selective for at least a portion of the plurality of genomic regions in the plurality of cfDNA molecules. In some embodiments, the probes are nucleic acid molecules having sequence complementarity with nucleic acid sequences of the plurality of genomic regions. In some embodiments, the nucleic acid molecules are primers or enrichment sequences. In some embodiments, the assaying comprises use of array hybridization or polymerase chain reaction (PCR), or nucleic acid sequencing.

In some embodiments, the method further comprises enriching the plurality of cfDNA molecules for at least a portion of the plurality of genomic regions. In some embodiments, the enrichment comprises amplifying the plurality of cfDNA molecules. For example, the plurality of cfDNA molecules may be amplified by selective amplification (e.g., by using a set of primers or probes comprising nucleic acid molecules having sequence complementarity with nucleic acid sequences of the plurality of genomic regions). Alternatively or in combination, the plurality of cfDNA molecules may be amplified by universal amplification (e.g., by using universal primers). In some embodiments, the enrichment comprises selectively isolating at least a portion (e.g., mononucleotides and/or dinucleotides) of the plurality of cfDNA molecules.

In some embodiments, the method of assessing tumor progression or tumor-non-progression in a subject comprises processing the plurality of counts to obtain a quantitative measure (e.g., a statistical measure) of deviation of the plurality of counts (as in 115). In some embodiments, the statistical measure of deviation comprises a z-score relative to a set of reference samples or a set of reference values (e.g., a set of baseline values). In some embodiments, the statistical measure of deviation is a "robust z-score" generated based on a median absolute deviation (MAD) generated by assaying samples obtained from an unaffected cohort of subjects. For the example, such a "robust z-score" may be generated by determining a difference (e.g., an absolute difference) between a deviation value of the test sample and the mean or median deviation value of a set of control samples (e.g., from an unaffected cohort), and dividing by the median absolute deviation (MAD) of the set of control samples from the unaffected cohort. The reference samples may be obtained from one or more subjects having a tumor progression and/or from subjects not having a tumor progression (e.g., subjects having a tumor non-progression or unaffected patients). The reference samples may be obtained from one or more subjects having a cancer type or from subjects not having a cancer type (e.g., breast cancer, cervical cancer, colorectal cancer, endometrial cancer, esophageal cancer, gastric cancer, hepatobiliary tract cancer, leukemia, liver cancer, lung cancer, lymphoma, ovarian cancer, pancreatic cancer, skin cancer, urinary tract cancer).

In some embodiments, the counts may be normalized or corrected. For example, the counts may be normalized and/or corrected to account for known biases in sequencing and library preparation and/or known biases in sequencing and library preparation. In some embodiments, a subset of the quantitative measures (e.g., statistical measures) of deviation may be filtered out, e.g., based on whether the deviations or changes in deviation are significantly different from those observed in unaffected subjects.

In some embodiments, the method of assessing tumor progression in a subject further comprises determining a tumor progression of the subject when the statistical measure of deviation of the plurality of counts satisfies a pre-determined criterion (as in 120). The statistical measure of deviation may comprise a z-score of the plurality of counts relative to a set of reference samples or a set of reference values (e.g., a set of baseline values). In some embodiments, the statistical measure of deviation is a "robust z-score" generated based on a mean or median value of the plurality of counts. In some embodiments, the pre-determined criterion is the absolute value of the mean z-score being greater than a pre-determined number. The pre-determined number may be about 0.1, about 0.2, about 0.5, about 1, about 1.5, about 2, about 2.5, about 3, about 3.5, about 4, about 4.5, about 5, or more than about 5.

In some embodiments, the plurality of genomic regions comprises mononucleotides and/or dinucleotides. The plurality of genomic regions may comprise at least about 10 distinct genomic regions, at least about 50 distinct genomic regions, at least about 100 distinct genomic regions, at least about 500 distinct genomic regions, at least about 1 thousand distinct genomic regions, at least about 5 thousand distinct genomic regions, at least about 10 thousand distinct genomic regions, at least about 50 thousand distinct genomic regions, at least about 100 thousand distinct genomic regions, at least about 500 thousand distinct genomic regions, at least about 1 million distinct genomic regions, at least about 2 million distinct genomic regions, at least about 3 million distinct genomic regions, at least about 4 million distinct genomic regions, at least about 5 million distinct genomic regions, at least about 10 million distinct genomic regions, at least about 15 million distinct genomic regions, at least about 20 million distinct genomic regions, at least about 25 million distinct genomic regions, at least about 30 million distinct genomic regions, or more than 30 million distinct genomic regions.

In some embodiments, the tumor progression of the subject is detected with a sensitivity of at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%.

In some embodiments, the tumor progression of the subject is detected with a specificity of at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%.

In some embodiments, the tumor progression of the subject is detected with a positive predictive value (PPV) of at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%.

In some embodiments, the tumor progression of the subject is detected with a negative predictive value (NPV) of at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%.

In some embodiments, the tumor progression of the subject is detected with an area under curve (AUC) of a receiver operator characteristic (ROC) of at least about 0.5, at least about 0.6, at least about 0.7, at least about 0.75, at least about 0.8, at least about 0.85, at least about 0.9, at least about 0.95, at least about 0.96, at least about 0.97, at least about 0.98, or at least about 0.99.

In some embodiments, the method of assessing tumor progression in a subject further comprises determining a tumor non-progression of the subject when the statistical measure of deviation of the plurality of counts does not satisfy the pre-determined criterion.

In some embodiments, the tumor non-progression of the subject is detected with a sensitivity of at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%.

In some embodiments, the tumor non-progression of the subject is detected with a specificity of at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%.

In some embodiments, the tumor non-progression of the subject is detected with a positive predictive value (PPV) of at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%.

In some embodiments, the tumor non-progression of the subject is detected with a negative predictive value (NPV) of at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%.

In some embodiments, the tumor non-progression of the subject is detected with an area under curve (AUC) of a receiver operator characteristic (ROC) of at least about 0.5, at least about 0.6, at least about 0.7, at least about 0.75, at least about 0.8, at least about 0.85, at least about 0.9, at least about 0.95, at least about 0.96, at least about 0.97, at least about 0.98, or at least about 0.99.

In some embodiments, the subject has been diagnosed with cancer. For example, the cancer may be one or more types, including: brain cancer, breast cancer, cervical cancer, colorectal cancer, endometrial cancer, esophageal cancer, gastric cancer, hepatobiliary tract cancer, leukemia, liver cancer, lung cancer, lymphoma, ovarian cancer, pancreatic cancer, skin cancer, or urinary tract cancer.

In some embodiments, the method further comprises, based on the determined tumor progression of the subject, administering a therapeutically effective amount of a treatment to treat the tumor of the subject. In some embodiments, the treatment comprises a chemotherapy, a radiation therapy, or an immunotherapy.

The tumor progression or tumor non-progression of a subject may be assessed to determine a diagnosis of a cancer, prognosis of a cancer, or an indication of progression or regression of a tumor in the subject. In addition, one or more clinical outcomes may be assigned based on the tumor progression or tumor non-progression assessment or monitoring (e.g., a difference in tumor progression or tumor non-progression status between two or more time points). Such clinical outcomes may include diagnosing the subject with a cancer comprising tumors of one or more types, diagnosing the subject with the cancer comprising tumors of one or more types and stages, prognosing the subject with the cancer (e.g., indicating a clinical course of treatment (e.g., surgery, chemotherapy, radiotherapy, targeted therapy, immunotherapy, or other treatment) for the subject, indicating another clinical course of action (e.g., no treatment, continued monitoring such as on a prescribed time interval basis, stopping a current treatment, switching to another treatment), or indicating an expected survival time for the subject.

In some embodiments, the method of assessing tumor progression of a subject further comprises determining whether the CID score meets a pre-determined criterion (e.g., being at least a pre-determined threshold, being greater than a pre-determined threshold, being at most a pre-determined threshold, or being less than a pre-determined threshold). The pre-determined threshold may be generated by performing the tumor progression or tumor non-progression assessment on one or more reference samples obtained or derived from one or more reference subjects (e.g., patients known to have a certain tumor type, patients known to have a certain tumor type of a certain stage, or healthy subjects not exhibiting any cancer) and identifying a suitable pre-determined threshold based on the tumor progression or tumor non-progression of the reference samples obtained or derived from the reference subjects.

The pre-determined threshold may be adjusted based on a desired sensitivity, specificity, positive predictive value (PPV), negative predictive value (NPV), or accuracy of assessing the tumor progression or tumor non-progression status of a subject. For example, the pre-determined threshold may be adjusted to be lower if a high sensitivity of assessing the tumor progression or tumor non-progression status of a subject is desired. Alternatively, the pre-determined threshold may be adjusted to be higher if a high specificity assessing the tumor progression or tumor non-progression status of a subject is desired. The pre-determined threshold may be adjusted so as to maximize the area under curve (AUC) of a receiver operator characteristic (ROC) of the reference samples obtained from the reference subjects. The pre-determined threshold may be adjusted so as to achieve a desired balance between false positives (FPs) and false negatives (FNs) in assessing obtained or derived from one or more reference subjects of a cancer comprising a tumor of one or more types.

In some embodiments, the method of assessing tumor progression or tumor non-progression further comprises repeating the assessment at a second later time point. The second time point may be chosen for a suitable comparison of tumor progression or tumor non-progression assessment relative to the first time point. Examples of second time points may correspond to a time after surgical resection, a time during treatment administration or after treatment administration to treat the cancer in the subject to monitor efficiency of the treatment, or a time after cancer is undetectable in the subject after treatment to monitor for residual disease or cancer recurrence in the subject.

In some embodiments, the method of assessing tumor progression or tumor non-progression further comprises determining a difference between the first tumor progression or tumor non-progression status and the second tumor progression or tumor non-progression, which difference is indicative of a progression or regression of a tumor of the subject. Alternatively or in combination, the method may further comprise generating, by a computer processor, a plot of the first tumor progression or tumor non-progression status and the second tumor progression or tumor non-progression status as a function of the first time point and the second time point, which plot is indicative of the progression or regression of the tumor of the subject. For example, the computer processor may generate a plot of the two or more tumor progression or tumor non-progression statuses on a y-axis against the times corresponding to the time of collection for the data corresponding to the two or more tumor progression or tumor non-progression statuses on an x-axis.

A determined difference or a plot illustrating a difference between the first tumor progression or tumor non-progression status and the second tumor progression or tumor non-progression status may be indicative of a progression or regression of a tumor of the subject. If the second tumor progression or tumor non-progression status is larger than the first tumor progression or tumor non-progression status, that difference may indicate, e.g., tumor progression, inefficacy of a treatment to the tumor in the subject, resistance of the tumor to an ongoing treatment, metastasis of the tumor to other sites in the subject, or residual disease or cancer recurrence in the subject. If the second tumor progression or tumor non-progression status is smaller than the first tumor progression or tumor non-progression status, that difference may indicate, e.g., tumor regression, efficacy of a surgical resection of the tumor in the subject, efficacy of a treatment to the tumor in the subject, or lack of residual disease or cancer recurrence in the subject.

After assessing and/or monitoring tumor progression or tumor non-progression status, one or more clinical outcomes may be assigned based on the tumor progression or tumor non-progression status assessment or monitoring (e.g., a difference in tumor progression or tumor non-progression status between two or more time points). Such clinical outcomes may include diagnosing the subject with a cancer comprising tumors of one or more types, diagnosing the subject with the cancer comprising tumors of one or more types and stages, prognosing the subject with the cancer (e.g., indicating a clinical course of treatment (e.g., surgery, chemotherapy, radiotherapy, targeted therapy, immunotherapy, or other treatment) for the subject, indicating another clinical course of action (e.g., no treatment, continued monitoring such as on a prescribed time interval basis, stopping a current treatment, switching to another treatment), or indicating an expected survival time for the subject.

Computer Systems

Figure 2:
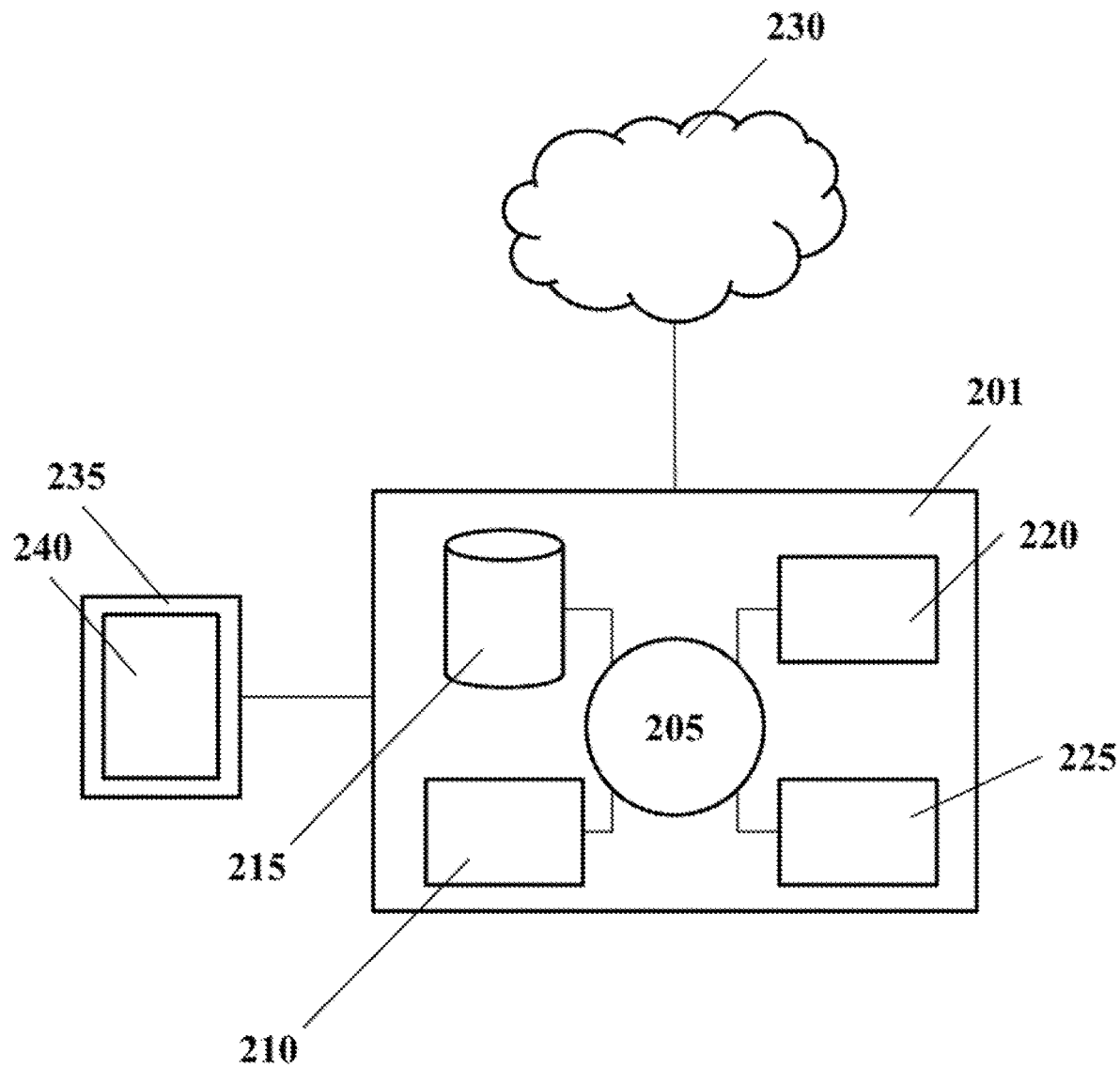
FIG. 2 illustrates a computer system that is programmed or otherwise configured to implement methods provided herein.

The present disclosure provides computer systems that are programmed to implement methods of the disclosure. FIG. 2 shows a computer system 201 that is programmed or otherwise configured to, for example, measure a count of a plurality of cell-free DNA (cfDNA) molecules at each of a plurality of genomic regions; process the plurality of counts measured at each of the plurality of genomic regions to obtain quantitative measures of deviation of the counts relative to reference values, to produce deviation scores; determine a difference between a set of deviation scores and a set of reference deviation scores to produce a set of changes in deviation (CID) values; apply a logarithmic transformation to a sum of CID values to produce a CID score; and detect a tumor progression of the subject when the CID score satisfies a pre-determined criterion. The computer system 201 can regulate various aspects of analysis, calculation, and generation of the present disclosure, such as, for example, measuring a count of a plurality of cell-free DNA (cfDNA) molecules at each of a plurality of genomic regions; processing the plurality of counts measured at each of the plurality of genomic regions to obtain quantitative measures of deviation of the counts relative to reference values, to produce deviation scores; determining a difference between a set of deviation scores and a set of reference deviation scores to produce a set of changes in deviation (CID) values; applying a logarithmic transformation to a sum of CID values to produce a CID score; and detecting a tumor progression of the subject when the CID score satisfies a pre-determined criterion. The computer system 201 can be an electronic device of a user or a computer system that is remotely located with respect to the electronic device. The electronic device can be a mobile electronic device.

The computer system 201 includes a central processing unit (CPU, also "processor" and "computer processor" herein) 205, which can be a single core or multi core processor, or a plurality of processors for parallel processing. The computer system 201 also includes memory or memory location 210 (e.g., random-access memory, read-only memory, flash memory), electronic storage unit 215 (e.g., hard disk), communication interface 220 (e.g., network adapter) for communicating with one or more other systems, and peripheral devices 225, such as cache, other memory, data storage and/or electronic display adapters. The memory 210, storage unit 215, interface 220 and peripheral devices 225 are in communication with the CPU 205 through a communication bus (solid lines), such as a motherboard. The storage unit 215 can be a data storage unit (or data repository) for storing data. The computer system 201 can be operatively coupled to a computer network ("network") 230 with the aid of the communication interface 220. The network 230 can be the Internet, an internet and/or extranet, or an intranet and/or extranet that is in communication with the Internet. The network 230 in some cases is a telecommunication and/or data network. The network 230 can include one or more computer servers, which can enable distributed computing, such as cloud computing. For example, one or more computer servers may enable cloud computing over the network 230 ("the cloud") to perform various aspects of analysis, calculation, and generation of the present disclosure, such as, for example, measuring a count of a plurality of cell-free DNA (cfDNA) molecules at each of a plurality of genomic regions; processing the plurality of counts measured at each of the plurality of genomic regions to obtain quantitative measures of deviation of the counts relative to reference values, to produce deviation scores; determining a difference between a set of deviation scores and a set of reference deviation scores to produce a set of changes in deviation (CID) values; applying a logarithmic transformation to a sum of CID values to produce a CID score; and detecting a tumor progression of the subject when the CID score satisfies a pre-determined criterion. Such cloud computing may be provided by cloud computing platforms such as, for example, Amazon Web Services (AWS), Microsoft Azure, Google Cloud Platform, and IBM cloud. The network 230, in some cases with the aid of the computer system 201, can implement a peer-to-peer network, which may enable devices coupled to the computer system 201 to behave as a client or a server.

The CPU 205 can execute a sequence of machine-readable instructions, which can be embodied in a program or software. The instructions may be stored in a memory location, such as the memory 210. The instructions can be directed to the CPU 205, which can subsequently program or otherwise configure the CPU 205 to implement methods of the present disclosure. Examples of operations performed by the CPU 205 can include fetch, decode, execute, and writeback.

The CPU 205 can be part of a circuit, such as an integrated circuit. One or more other components of the system 201 can be included in the circuit. In some cases, the circuit is an application specific integrated circuit (ASIC).

The storage unit 215 can store files, such as drivers, libraries and saved programs. The storage unit 215 can store user data, e.g., user preferences and user programs. The computer system 201 in some cases can include one or more additional data storage units that are external to the computer system 201, such as located on a remote server that is in communication with the computer system 201 through an intranet or the Internet.

The computer system 201 can communicate with one or more remote computer systems through the network 230. For instance, the computer system 201 can communicate with a remote computer system of a user (e.g., a physician, a nurse, a caretaker, a patient, or a subject). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 201 via the network 230.

Methods as described herein can be implemented by way of machine (e.g., computer processor) executable code stored on an electronic storage location of the computer system 201, such as, for example, on the memory 210 or electronic storage unit 215. The machine executable or machine readable code can be provided in the form of software. During use, the code can be executed by the processor 205. In some cases, the code can be retrieved from the storage unit 215 and stored on the memory 210 for ready access by the processor 205. In some situations, the electronic storage unit 215 can be precluded, and machine-executable instructions are stored on memory 210.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 201 can include or be in communication with an electronic display 235 that comprises a user interface (UI) 240 for providing, for example, determined quantitative measures generated from a blood sample of a subject, statistical measures of deviation of the counts, and determined tumor progression or tumor non-progression of the subject. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 205. The algorithm can, for example, measure a count of a plurality of cell-free DNA (cfDNA) molecules at each of a plurality of genomic regions; process the plurality of counts measured at each of the plurality of genomic regions to obtain quantitative measures of deviation of the counts relative to reference values, to produce deviation scores; determine a difference between a set of deviation scores and a set of reference deviation scores to produce a set of changes in deviation (CID) values; apply a logarithmic transformation to a sum of CID values to produce a CID score; and detect a tumor progression of the subject when the CID score satisfies a pre-determined criterion.

EXAMPLES

Example 1: Tumor Progression Determination by Whole Genome Sequencing of Patient Samples Tumor progression is determined for each of a set of 55 subjects with cancer and 27 control subjects without cancer. The affected patients all have advanced stage cancers, mostly breast and lung, but also including bladder, colon, prostate, rectal, renal and stomach cancers. Each patient was starting a new therapy, either after failure of a previous therapy or for a newly diagnosed disease. The patients were evaluated for progression based on RECIST criteria as well as clinical progressions.

For each of the set of subjects, cfDNA samples are obtained for at least two time points, including one baseline time point at or around the commencement of treatment, and next-generation sequencing (NGS) data is produced for each of the cfDNA samples at a sequencing depth of about 25× coverage. The method for assessing tumor progression is applied to generate predictions of tumor progression from the cfDNA data set.

At each timepoint, cell-free plasma DNA is sequenced and aligned to the reference genome. The number of reads aligning to each of a plurality of 1 megabase (MB) non-overlapping genomic windows (or bins) is counted in the human genome with the following exceptions: (1) chromosomes X and Y to reduce sex bias; (2) chromosome 19 because it is known to be noisy; and (3) centromeric and telomeric regions in each chromosome. Each sequenced library thus produces 2347 counts, one per 1 MB bin included in the score. Next, the counts are corrected for GC content and mappability bias using LOESS regression. The counts are then normalized relative to a cohort of unaffected patients (e.g., patients without cancer), and the normalized counts are log transformed (e.g., by applying a logarithmic transformation). The absolute value of the corrected and normalized counts is calculated to determine their deviation, that is, how much they differ from the mean of the unaffected cohort.

For longitudinal comparison between two timepoints (e.g., analyzing two samples collected from the same subject at two different timepoints), the difference between the two deviations is computed. Optionally, the difference may be normalized, such as by dividing by the median absolute deviation (MAD) of the unaffected cohort. The CID score is computed as the sum of changes in deviation after filtering out (e.g., excluding) bins where the change is less than the maximum change among all bins among all longitudinal pairs (e.g., pairs of samples collected from the same subject at two different timepoints) in the unaffected cohort. A tumor progression is detected in the subject if the CID score is greater than zero, and a tumor non-progression is detected otherwise. Such analysis using CID scores can predict progression well in advance of standard of care imaging (e.g., an average of at least about 7 days, at least about 14 days, at least about 21 days, at least about 30 days, at least about 45 days, at least about 60 days, at least about 90 days, or more).

More generally, the CID score can be computed as follows:

First, the number of sequence reads is counted in non-overlapping genomic windows of some size. The non-overlapping genomic windows may be equally sized or differently sized, such as about 10 kilobases (kb), about 25 kb, about 50 kb, about 100 kb, about 250 kb, about 500 kb, about 1 megabase (Mb), about 2 Mb, about 5 Mb, about 10 Mb, or more. The non-overlapping genomic windows may correspond to chromosomal arms or full chromosomes. Some genomic regions may be excluded from the analysis, such as sex chromosomes (X and Y, to eliminate sex bias), centromeric regions, telomeric regions, chromosomes with high variance between replicates (e.g., ch19), chromosomes with extreme sequence content (e.g. high GC content), or a combination thereof. The non-overlapping genomic windows may comprise CNA loci and/or cancer-associated loci, such as loci selected from The Cancer Genome Atlas (TCGA) or Catalogue of Somatic Mutations in cancer (COSMIC).

Next, the read counts are normalized and corrected to account for technical factors, such as biases in sequencing and library preparation (e.g., mappability bias and GC content), total sequencing depth, and (2) the degree of variance in unaffected samples. For example, the reads can be normalized by the total number of reads per sample (equivalent to normalizing by sequencing depth). As another example, the reads can be corrected for bias due to GC-content and mappability (e.g., using LOESS regression). As another example, the reads can be normalized for the variation in unaffected control samples, by dividing the pre-log2 transformed counts by the median. As another example, the reads can be normalized by applying a log2 transform to the counts. As another example, the reads can be normalized for the variation in unaffected control samples by subtracting the projection onto some number of principal components of the unaffected control samples (e.g., PCA correction).

Next, the deviation per sample per timepoint is determined, e.g., by converting normalized counts to deviations to quantify how each per-timepoint library differs from unaffected subjects. For example, the deviation can be computed for each sample and timepoint by calculating the absolute value of the robust z-score of counts in each window relative to the unaffected control samples. As another example, the deviation can be computed for each sample and timepoint by calculating the absolute value of z-score relative to unaffected control samples. As another example, the deviation can be computed for each sample and timepoint by calculating a signed value (e.g., without taking the absolute value) by using an alternate method for computing the change in deviation.

Next, longitudinal changes in deviation between two timepoints are determined. For example, the longitudinal changes in deviation between two timepoints can be computed by determining the change in deviation given by the difference of the deviations at two timepoints (e.g., a first deviation at a first timepoint minus an initial deviation at an initial timepoint). As another example, the longitudinal changes in deviation between two timepoints can be computed by determining the change in deviation given as a ratio rather than difference. As another example, the longitudinal changes in deviation between two timepoints can be computed by determining the change in signed deviation by excluding bins where the sign changes between timepoints. As another example, the longitudinal changes in deviation between two timepoints can be computed by determining the change in signed deviation by setting a floor value of 0 (e.g., setting negative values to 0).

Next, bins having changes within a normal range are filtered (e.g., bins where the change is not significantly different from the longitudinal change observed in unaffected subjects). For example, bins can be filtered when the determined longitudinal change for a given bin is not greater than the largest longitudinal change observed in any bin in longitudinal pairs of unaffected control samples. As another example, bins can be filtered based on a percentile cutoff (e.g., the 90th to the 99th percentile) of the change observed in any bin in longitudinal pairs of unaffected control samples. As another example, bins can be filtered based on the largest longitudinal changes observed per bin in longitudinal pairs of unaffected control samples, thereby having a different filtering threshold for each bin. As another example, bins can be filtered based on a percentile cutoff (e.g., the 90th to the 99th percentile) of the changes observed per bin in longitudinal pairs of unaffected control samples, thereby having a different filtering threshold for each bin. As another example, bins can be filtered when the determined longitudinal change for a given bin is not at least about 0.5, at least about 1, at least about 1.5, at least about 2, at least about 2.5, at least about 3, at least about 3.5, or at least about 4 standard deviations greater than the mean of the longitudinal change observed in any bin in longitudinal pairs of unaffected control samples. As another example, bins can be filtered when the determined longitudinal change for a given bin is not at least about 0.5, at least about 1, at least about 1.5, at least about 2, at least about 2.5, at least about 3, at least about 3.5, or at least about 4 standard deviations greater than the mean of longitudinal change observed per bin in longitudinal pairs of unaffected control samples, thereby having a different filtering threshold for each bin.

Next, change in deviation (CID) scores are determined for each sample and timepoint, e.g., by aggregating the per-bin changes in deviation into a genome-wide score. For example, the CID scores can be determined by determining a sum of the bins remaining after filtering, and optionally applying a logarithmic transform to the sum. The logarithmic transform can be a logarithm (log) such as natural logarithm (ln), a logarithm base 10 (log10), or a logarithm base 2 (log2). The logarithmic transform can be a log-modulus that preserves sign, e.g., $L(x)=sign(x)*log(|x|+1)$. As another example, the CID scores can be determined by determining a weighted sum of bins remaining after filtering (e.g., where bin weights are computed via some procedure to determine bin importance), and optionally applying a logarithmic transform to the sum. The logarithmic transform can be a logarithm (log) such as natural logarithm (ln), a logarithm base 10 (log10), or a logarithm base 2 (log2). The logarithmic transform can be a log-modulus that preserves sign, e.g., $L(x)=sign(x)*log(|x|+1)$. As another example, the CID scores can be determined by setting a score to 0 if fewer than a given number of bins remains after filtering, thereby preventing scores from being computed without high confidence based on a minimum threshold number of bins.

Next, samples can be classified using discrete labels, such as "Progression" and "Non-Progression," based on their CID scores. At this point, which fraction of the patient's genome that appears more aberrant at a later time point and which fraction appears less aberrant at the later time point have been determined. A threshold can be applied to call patients as having a progression if more of the genome is aberrant at the later timepoint (equivalent to a score greater than 0), e.g., a progression. For example, the classifying can be performed using the natural decision threshold of 0 or those learned from data. As another example, a higher or lower threshold can be used in order to optimize the sensitivity, specificity, and no call rate. As another example, positive and negative changes can be weighted differently (e.g., positive changes could be weighted more to account for the fact that any increase is an indicator of poor outcome). As another example, individual bins can be weighted separately based on how aberrant the bin is. In some cases, an additional label called "No-Call" can be included, and samples can be classified using two score thresholds, whereby scores above a positive score X are labeled "Progression," scores below a negative score Y are labeled "Non-Progression," and scores between X and Y are labeled "No-Call."

Example 2: Longitudinal Tumor Progression Determination at Two Timepoints

Tumor progression is assessed in each of a plurality of subjects longitudinally at two different timepoints. A log-transformed plot of CID scores for the plurality of subjects is generated at a first timepoint (timepoint 1). Next, a log-transformed plot of CID scores for the same plurality of subjects is generated at a second timepoint (timepoint 2).

The tumor progression assessment at timepoint 1 has a low sensitivity of about 50% and a high specificity of about 95%. In contrast, the tumor progression assessment at timepoint 2 has a higher sensitivity of about 65% and a high specificity of about 95%, which meets clinical specifications. Thus, tumor progression is detected in more subjects of the plurality of subjects in timepoint 2 as compared to timepoint 1.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for monitoring tumor progression or tumor non-progression of a tumor of a subject, comprising:
   measuring, by a processor, a count of a plurality of cell-free DNA (cfDNA) molecules at each of a plurality of genomic regions, wherein the plurality of cfDNA molecules is obtained or derived from a bodily fluid sample of the subject at a first timepoint;
   processing, by the processor, the plurality of cfDNA counts measured at each of the plurality of genomic regions to obtain quantitative measures of deviation of the plurality of counts relative to a plurality of reference values to produce a plurality of deviation scores of the subject, wherein the plurality of reference values comprises an additional plurality of counts obtained from additional cfDNA molecules obtained or derived from additional bodily fluid samples of additional subjects that are unaffected by cancer or without a diagnosis of cancer;
   determining, by the processor, a difference between the plurality of deviation scores and a plurality of reference deviation scores to produce a plurality of changes in deviation (CID) values, wherein the reference deviation scores are a baseline set of deviation values generated from additional subjects that are unaffected by cancer or without a diagnosis of cancer, and applying a logarithmic transformation to a sum of the plurality of CID values to produce a CID score;
   measuring, by the processor, a second count of a second plurality of cfDNA molecules at each of the plurality of genomic regions, wherein the second plurality of cfDNA molecules is obtained or derived from a bodily fluid sample of the subject at a second timepoint after the first timepoint;

processing, by the processor, the plurality of second counts measured at each of the plurality of genomic regions to obtain second quantitative measures of deviation of the second plurality of counts relative to the plurality of reference values to produce a second plurality of deviation scores;

determining, by the processor, a difference between the second plurality of deviation scores and the second plurality of reference deviation scores to produce a second plurality of changes in deviation (CID) values, and applying a logarithmic transformation to a sum of the second plurality of CID values to produce a second CID score; and determining, by the processor, a difference between the first and second CID scores, said difference being indicative of tumor progression or tumor non-progression of the tumor of the subject, wherein when the difference between the first and second CID scores is greater than zero, the difference is indicative of tumor progression.

2. The method of claim 1, wherein the bodily fluid sample is selected from the group consisting of: blood, serum, plasma, vitreous fluid, sputum, urine, tears, perspiration, saliva, semen, mucosal excretions, mucus, spinal fluid, cerebrospinal fluid (CSF), pleural fluid, peritoneal fluid, amniotic fluid, and lymph fluid.

3. The method of claim 1, wherein measuring the plurality of cfDNA counts comprises sequencing the plurality of cfDNA molecules to generate sequencing reads at each of the plurality of genomic regions in the plurality of cfDNA molecules.

4. The method of claim 3, wherein the sequencing comprises whole genome sequencing (WGS).

5. The method of claim 4, wherein the sequencing is performed at a depth of no more than about 25×, no more than about 10×, no more than about 8×, or no more than about 6×.

6. The method of claim 3, further comprising aligning the plurality of sequence reads to a reference genome of the same species, thereby producing a plurality of aligned sequence reads.

7. The method of claim 1, wherein measuring the plurality of counts comprises performing binding measurements of the plurality of cfDNA molecules at each of the plurality of genomic regions.

8. The method of claim 1, further comprising enriching the plurality of cfDNA molecules for at least a subset of the plurality of genomic regions.

9. The method of claim 8, wherein the enrichment comprises amplifying the plurality of cfDNA molecules and/or selectively isolating at least a portion of the plurality of cfDNA molecules.

10. The method of claim 9, wherein the amplification comprises selective amplification and/or universal amplification.

11. The method of claim 9, wherein selectively isolating the portion of the plurality of cfDNA molecules comprises using a plurality of probes, each of the plurality of probes having sequence complementarity with at least a portion of a genomic region of the plurality of genomic regions.

12. The method of claim 9, wherein the portion of the plurality of cfDNA molecules comprises a tumor marker locus and/or a plurality of tumor marker loci.

13. The method of claim 12, wherein the plurality of tumor marker loci comprises one or more loci selected from The Cancer Genome Atlas (TCGA) or Catalogue of Somatic Mutations in cancer (COSMIC).

14. The method of claim 3, wherein measuring the plurality of cfDNA counts further comprises counting a number of the plurality of sequence reads aligning to each of the plurality of genomic regions.

15. The method of claim 1, further comprising correcting the plurality of cfDNA counts for GC content and/or mappability bias.

16. The method of claim 15, wherein the correcting comprises using a LOESS regression.

17. The method of claim 1, wherein the quantitative measure of deviation is a statistical measure of deviation of the plurality of counts relative to the plurality of reference values, or a weighted combination thereof.

18. The method of claim 17, further comprising filtering out a subset of the plurality of CID values that meet a pre-determined criterion.

19. The method of claim 18, further comprising filtering out a CID value of the plurality of CID values when the difference between the deviation score and the reference deviation score comprises a difference of no more than about 1 standard deviation, no more than about 2 standard deviations, or no more than about 3 standard deviations.

20. The method of claim 18, further comprising calculating a sum of the filtered plurality of CID values.

21. The method of claim 20, wherein calculating the sum comprises calculating a weighted sum of the filtered plurality of CID values.

22. The method of claim 17, wherein determining the difference comprises calculating a subtraction between each of the plurality of deviation scores of the subject and a corresponding reference deviation score of the plurality of reference deviation scores.

23. The method of claim 22, further comprising dividing a subtraction of each of the plurality of deviation scores of the subject or the plurality of CID values by a corresponding median absolute deviance of the plurality of reference values.

24. The method of claim 1, wherein the plurality of genomic regions comprises non-overlapping genomic regions of a reference genome of the same species having a pre-determined size.

25. The method of claim 24, wherein the pre-determined size is about 50 kilobases (kb), about 100 kb, about 200 kb, about 500 kb, about 1 megabases (Mb), about 2 Mb, about 5 Mb, or about 10 Mb.

26. The method of claim 24, wherein the plurality of genomic regions excludes genomic regions of the reference genome corresponding to one or more of: sex chromosomes, chromosome 19, centromere regions in each chromosome, and telomere regions in each chromosome.

27. The method of claim 1, wherein the plurality of genomic regions comprises at least about 1,000 distinct genomic regions or at least about 2,000 distinct genomic regions.

28. The method of claim 1, wherein detecting the tumor progression of the subject has a sensitivity of at least about 50%, at least about 70%, or at least about 90%.

29. The method of claim 1, wherein detecting the tumor progression of the subject has a specificity of at least about 50%, at least about 70%, or at least about 90%.

30. The method of claim 1, wherein the method is characterized by:

detecting the tumor progression of the subject with a positive predictive value (PPV) of at least about 50%, at least about 70%, or at least about 90%;
detecting the tumor progression of the subject with a negative predictive value (NPV) of at least about 50%, at least about 70%, or at least about 90%; and/or
detecting the tumor progression of the subject with an area under the curve (AUC) of at least about 0.60, at least about 0.75, or at least about 0.90.

31. The method of claim 1, wherein when the difference between the first and second CID scores is zero, the difference is indicative of tumor non-progression.

32. The method of claim 1, wherein the subject has been diagnosed with cancer.

33. The method of claim 32, further comprising, based on the determined tumor progression of the subject, administering a therapeutically effective dose of a treatment to treat the cancer of the subject.

34. The method of claim 33, wherein the treatment comprises surgery, chemotherapy, radiation therapy, targeted therapy, or immunotherapy.

35. A system, comprising a controller comprising or capable of accessing, a non-transitory computer-readable medium comprising machine-executable instructions which, upon execution by one or more computer processors, perform a method for monitoring tumor progression or tumor non-progression of a tumor of a subject, the method comprising:
measuring a count of a plurality of cell-free DNA (cfDNA) molecules at each of a plurality of genomic regions, wherein the plurality of cfDNA molecules is obtained or derived from a bodily fluid sample of the subject at a first timepoint;
processing the plurality of counts measured at each of the plurality of genomic regions to obtain quantitative measures of deviation of the plurality of counts relative to a plurality of reference values to produce a plurality of deviation scores, wherein the plurality of reference values comprises an additional plurality of counts obtained from additional cfDNA molecules obtained or derived from additional bodily fluid samples of additional subjects that are unaffected by cancer or without a diagnosis of cancer;
determining a difference between the plurality of deviation scores and a plurality of reference deviation scores to produce a plurality of changes in deviation (CID) values, wherein the reference deviation scores are a baseline set of deviation values generated from additional subjects that are unaffected by cancer or without a diagnosis of cancer, and applying a logarithmic transformation to a sum of the plurality of CID values to produce a CID score;
measuring a second count of a second plurality of cfDNA molecules at each of the plurality of genomic regions, wherein the second plurality of cfDNA molecules is obtained or derived from a bodily fluid sample of the subject at a second timepoint after the first timepoint;
processing the plurality of second counts measured at each of the plurality of genomic regions to obtain second quantitative measures of deviation of the second plurality of counts relative to the plurality of reference values to produce a second plurality of deviation scores;
determining a difference between the second plurality of deviation scores and the second plurality of reference deviation scores to produce a second plurality of changes in deviation (CID) values, and applying a logarithmic transformation to a sum of the second plurality of CID values to produce a second CID score; and
determining a difference between the first and second CID scores, said difference being indicative of tumor progression or tumor non-progression of the tumor of the subject, wherein when the difference between the first and second CID scores is greater than zero, the difference is indicative of tumor progression.

36. The method of claim 1, wherein the plurality of genomic regions represents a plurality of tumor markers.

37. The method of claim 1, wherein the first timepoint represents a baseline timepoint at or around commencement of a treatment.

38. The method of claim 1, wherein a duration between the first and second timepoints represents a course of treatment for the tumor of the subject or a time during or after treatment administration for the tumor of the subject.

39. The method of claim 1, wherein a duration between the first and second timepoints represents a monitoring period after surgical resection or other treatment of the tumor.

40. The method of claim 1, wherein the first timepoint represents a timepoint in which cancer is undetectable in the subject after treatment, and the method is used to monitor for residual disease or cancer recurrence at the second timepoint.

41. The method of claim 1, wherein the bodily fluid sample is whole blood sample.

* * * * *